(12) United States Patent
Voic et al.

(10) Patent No.: US 8,109,925 B2
(45) Date of Patent: Feb. 7, 2012

(54) TREATMENT OF BREAST DISEASE WITH VIBRATING DEVICE

(75) Inventors: Dan Voic, Cedar Grove, NJ (US);
Ronald R. Manna, Valley Stream, NY (US)

(73) Assignee: Misonix Incorporated, Farmingdale, NY (US)

( * ) Notice: Subject to any disclaimer, the term of this patent is extended or adjusted under 35 U.S.C. 154(b) by 1260 days.

(21) Appl. No.: 11/805,940

(22) Filed: May 25, 2007

(65) Prior Publication Data
US 2008/0294044 A1    Nov. 27, 2008

(51) Int. Cl.
*A61B 18/04* (2006.01)
(52) U.S. Cl. .......................... 606/27; 606/169
(58) Field of Classification Search ............ 606/34, 606/37, 41, 169; 604/22
See application file for complete search history.

(56) References Cited

U.S. PATENT DOCUMENTS

| | | | | |
|---|---|---|---|---|
| 5,169,397 A * | 12/1992 | Sakashita et al. | ............... | 606/27 |
| 5,334,183 A * | 8/1994 | Wuchinich | ....................... | 606/46 |
| 6,102,885 A * | 8/2000 | Bass | ............................... | 604/22 |
| 6,306,132 B1 * | 10/2001 | Moorman et al. | ............... | 606/41 |

* cited by examiner

*Primary Examiner* — Michael Peffley
*Assistant Examiner* — Daniel Fowler
(74) *Attorney, Agent, or Firm* — R. Neil Sudol; Henry D. Coleman; William J. Sapone

(57) ABSTRACT

An elongate probe, with a suction channel extending longitudinally along the probe, is inserted into a patient so that a distal tip of the probe is in contact with a fibroid mass inside the patient. Thereafter the probe is ultrasonically vibrated so that the distal tip has an excursion amplitude or distance greater than 275 microns. During probe vibration, suction is applied to the channel at a vacuum level greater than 24" Hg to thereby maintain the target tissue mass in engagement with the distal tip during the vibrating of the probe and enable ablation of at least a selectable portion of the target tissue mass.

11 Claims, 1 Drawing Sheet

TREATMENT OF BREAST DISEASE WITH VIBRATING DEVICE

BACKGROUND OF THE INVENTION

This invention relates to a surgical technique and an associated instrument or device. More particularly, this invention relates in part to a method of using tools vibrating at ultrasonic frequencies for treating specific diseases of the human body.

Human breast disease in both males and females can have catastrophic consequence not only for the patients but to their families, for many years even after the untimely death of the loved one. Because of the activism of many groups, the funding levels of research into the causes and treatments of breast disease is one of the highest today. Although great strides have been made in the diagnosis and treatment of breast cancer in humans and the survival rates have been drastically improved over those of even twenty years ago, much work needs to be done to improve both the diagnostic techniques and treatment of these maladies.

One of the issues is the characterization of lesions within the body after the initial discovery by palpation, mammography or other radiological diagnosis tools. A mass that shows up by any of these techniques may be a benign fatty deposit, a hard fibroid or a cancerous lesion. The long-term prognosis for the patient is vastly different for each of these, of course. A biopsy will generally be taken of the lesion with a standard cannula and then sent to a pathologist for examination. Where cancer cells have been found in the biopsy sample, a lumpectomy or mastectomy will be performed. As an alternative, radiation treatments and/or chemotherapy may be used in some cases.

Where the biopsy is negative for cancer cells or is inconclusive, a period of watchful waiting is generally chosen. Here the patient is told to wait and to schedule periodic visits for reexamination, to see if the lesion changes size or shape. If it does, another biopsy will be performed to determine if cancer cells are present or not. This repeated examination and the anxiety associated with the possibilities of prognosis is akin to living under the Sword of Damocles for many people. They would prefer that the lump or mass be removed immediately and be done with it. However, this is not always possible without major surgery to get to the site and remove the mass via open field procedures. The scars and the resultant effect of changing the shape of the breast could lead to esthetic concerns in women especially, which will lead to further cosmetic surgery to correct these abnormalities. Insurance companies generally will balk at having to pay the high costs associated with major surgery for a diagnosis which is not immediately threatening to the life or health of the patient. Even when payment is available, the time and potential consequences of the treatment may make the operation unacceptable to the patient, who may delay the procedure until such time as it is absolutely necessary, notwithstanding the psychological consequences.

If a minimally invasive technique existed which would allow the surgeon to go in and remove the mass totally without resorting to open field procedures, more people would opt for quick excision of the mass at its discovery. This would improve quality of life of the patient and result in fewer precancerous masses that become malignant and ruin lives in the process. Attributes of the device and method would be a minimal incision size, full visibility of the target lesion, and the ability to remove any or all of the suspect tissue at the surgeon's discretion, as well as simplicity of operation and an inexpensive cost that would encourage widespread use in clinics and outlying hospitals.

It is therefore desired to create hardware and associated methods that will allow the dissection and aspiration of a tissue volume from the body consistently, with minimal trauma and esthetic impact.

OBJECTS OF THE INVENTION

An object of this invention is to provide a surgical method to allow clinicians to remove tissue masses from the body, in particular the human breast, under minimally invasive conditions.

Another object of this invention is to describe a hardware embodiment that will provide a means to allow a surgeon to remove tissue mass from the body with minimal blood loss.

Another object of the invention is to provide a device or apparatus that allows aspiration of the ablated tissue.

A further object of the invention is to provide a device or apparatus that allows tissue to be removed with enough intact cells to allow pathologic identification of tissue mass type.

An additional object of the invention is to provide such a method and/or apparatus that enables or facilitates visualization to allow precise targeting of a tissue mass and confirmation of successful removal.

Another object of the invention is to provide means to apply cauterizing energy to the tip of the probe either simultaneously or separately from ultrasound energy Yet another object of the invention is to provide a method of use of all of the hardware embodiments to accomplish stated goals.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A surgical method in accordance with the present invention uses a tool vibrating at frequencies in the ultrasound range to ablate tissue at a distal end of the tool. Such tools have been used in general and neurosurgery for many years. The current embodiment allows for the removal of tissue mass deep within the body while minimizing collateral tissue damage and reducing the need for a long incision, thereby reducing residual scarring.

A piezoelectric or magnetostrictive type transducer can be used to drive an elongated cannulated probe. The probe may be designed and built in lengths required for deep access to the tumor site by means known to the art. The probe may have a single cannula or be machined with multiple cannulae.

As is known to the art, when an alternating electric voltage and current excites a transducer and probe combination, the assembly will begin to vibrate as a unit. A distal surface will have an amplitude of vibration proportional to the input signal. The actual amplitude is a function of the geometry of the transducer and cannula. The device may be designed to have (a) an amplitude which is purely longitudinal, that is, having an axis of vibration which is parallel to the long axis of the device, (b) an amplitude that is purely transverse, i.e., perpendicular to the long axis, (c) an amplitude that is angular, i.e., in the case of a torsional vibration, or (d) any combination of the three.

Historically, ultrasound devices have been shown to be more effective at ablating tissues with a high liquid content. Such tissues include brain tissue, adipose tissue, liver tissue, etc. Tissues with a long cell structure, like heart muscle, have been harder to ablate. Fibrous tissue tissues have been the hardest to treat, leading to the belief that ultrasound cannot be used for such applications. The present invention is founded in part on the surprising and unexpected observation that fibrous tissues may be treated with ultrasound when proper operating parameters are specified and equipment is designed to provide them.

In order to treat hard fibroids of the breast, an ultrasound probe, whether cannulated or not, requires amplitudes greater than 275 microns peak to peak at the distal end to disrupt the tissue and dissect it from the body. This is a critical value. Amplitudes below this level have been shown not to be effective in ablating fibrous tissue.

In addition, a high level of suction is required to hold the tissue against the vibrating face of the probe. If suction is not present, the probe actually moves the tissue away from the operating face. Since the tissue acts as a damped mass spring combination, the tissue response is slower than that of the vibrating face and the tissue cannot follow the probe back and forth. This disconnection between the tissue and the vibrating tool reduces effectiveness and limits the ablation potential of the device. It has also been found that the vacuum level must be greater than a critical value of approximately 24" Hg, that is, the vacuum pump must provide a very low absolute vacuum, preferably as close to 29" Hg as possible.

As indicated above, the prior art teaches that it is not possible to remove fibroid masses from the breast through the use of ultrasound. In view of the current knowledge and experience of those in the art, it is surprising and unexpected to find that ultrasonic vibration can in fact be used to ablate and excise breast fibroid masses.

The method of use of the device may be described as follows. The clinician visualizes the area to be treated with standard diagnostic means, such as, but not limited to, diagnostic ultrasound or fluoroscopy. An incision site is chosen which will allow the probe to be introduced under the skin. The probe is then inserted and, while under visualization, the ultrasound energy is activated and the distal end of the probe is advanced to the lesion site.

More specifically, a surgical method in accordance with the present invention comprises (1) providing an elongate probe and a suction channel extending longitudinally along the probe, (2) inserting a distal end portion of the probe into a patient so that a distal tip of the probe is in contact with a target tissue mass inside the patient, (3) after contact of the distal tip with the target tissue mass, ultrasonically vibrating the probe so that the distal tip has an excursion amplitude or distance greater than 275 microns, and (4) during the vibrating of the probe, applying suction to the channel at a vacuum level greater than 24" Hg to maintain the target tissue mass in engagement with the distal tip during the vibrating of the probe and enable ablation of at least a selectable portion of the target tissue mass.

The clinician moves the tip of the probe in the target area to remove as much tissue as is desired. The ultrasound energy is subsequently turned off and the probe removed. The incision is closed by standard methods.

The channel may be formed as a bore passing longitudinally through the probe. In that case, a suction source is connected to the probe so as to communicate with the channel. Alternatively, the channel may be formed by a sheath or cannula. In that event, the inserting of the distal end portion of the probe into the patient includes deploying the probe so that it extends longitudinally through the channel.

Pursuant to an additional feature of the present invention, the method further comprises extracting a biopsy sample of the target tissue mass while the distal end portion of the probe is disposed in the patient. The biopsy sample may be taken during or prior to total fibroid ablation. In one embodiment, the probe is advanced to the fibroid and the ultrasound energy is then stopped. The extraction process entails (a) inserting a biopsy cannula into the channel, (b) advancing the cannula through the channel, (c) inserting a distal end of the cannula into the target tissue mass, (d) subsequently withdrawing the cannula from the channel and from the patient, and (d) connecting or reconnecting a suction source to the probe. The operation would then continue until the tissue mass was removed.

In an alternative embodiment of obtaining a biopsy, the extracting of the biopsy sample may be accomplished by providing a biopsy trap in a suction line communicating with the channel, thereby trapping tissue during the ultrasonic vibrating of the probe tip. This improvement can obviate the need for a separate biopsy process.

Pursuant to another feature of the present invention, the method further comprises conducting electrical current to the distal tip and from the distal tip into tissues of the patient to effect a cauterization of bleeding blood vessels. Cauterization may be implemented by the conduction of RF cautery or cutting currents to the probe tip. Cauterization allows bleeders to be treated without removing the ultrasound device. The RF energy may be supplied by commercially available electrosurgical generators and operatively connected to the tip by methods known to the art. (See, for instance, ultrasonic surgical instruments disclosed in U.S. Pat. Nos. 6,736,814 and 6,648,839.) This RF energy may be applied simultaneously or separately from the ultrasound energy.

In the case of a long probes passing though a substantial length of tissue, a non-electrically conductive sheath may be required to cover the probe to isolate it from the body so that the RF energy application may be made precisely. Conversely, the probe may be coated with non-conductive materials such as polytetrafluoroethylene (Teflon™) to achieve the same result.

Irrigation fluids such as saline or sterile water may be provided at the tip of the probe to enhance cavitation forces, irrigate and cool the operative site and provide a carrier fluid for the ablated material, which allows complete removal of all disrupted tissue. This is particularly important in cases of malignancies. Such irrigation fluid may be medicated with antibiotics, anesthetics, or other compounds that may be medically useful.

The method may further comprise scanning the patient in a region about the target tissue mass and generating an image of the target tissue mass on a display. In that case, the inserting of the probe into the patient is performed under visualization.

The probe may be introduced to the patient and moved to the desired surgical site by any suitable technique. One technique that works well is to move the probe towards the target fibrous tissue mass while ultrasonically vibrating the probe. The ultrasonic vibration eases the insertion procedure.

A surgical apparatus comprises, in accordance with the present invention, (i) an elongate probe having a distal tip, (ii) a channel extending longitudinally along the probe, (iii) a transducer assembly operatively connected to the probe for ultrasonically vibrating the probe, and (iv) a vacuum generator operatively connectable to the channel to apply suction to the channel at a vacuum level greater than 24" Hg to maintain a target tissue mass in engagement with the distal tip during the vibrating of the probe and enable ablation of at least a selectable portion of the target tissue mass. The probe and the transducer assembly are configured so that the distal tip of the probe has an excursion amplitude or distance greater than 275 microns.

The apparatus may additionally comprise (A) an electrical circuit for conducting current to the distal tip and from the distal tip into tissues of the patient to effect a cauterization of bleeding blood vessels, and/or (B) an irrigation conduit and associated reservoir for feeding an irrigation fluid to the probe tip to enhance cavitation forces, irrigate and cool the operative site and provide a carrier for ablated tissue.

The suction channel may extend inside the probe, or surround the probe when a sheath is provided. In the latter case, the probe may take the form of a semi-rigid or totally flexible wire or tube that can be activated by ultrasound energy in lieu of a rigid cannulated probe. Here the clinician may place a standard cannula into the body under direct visualization. The ultrasound wire would then be introduced into the cannula and the distal end advanced to the tumor site. The ultrasound would be turned on and the operation would be performed as describe herein. Such devices may double as the biopsy tool. RF energy and irrigation could also be provided.

Although the devices and methods described herein have been shown to have application in treating human breast disease, they would have applicability to other organs and sites within the human body as well. Other target tissues of particular interest are uterine fibroids or myomas.

DETAILED DESCRIPTION

Figure 1:
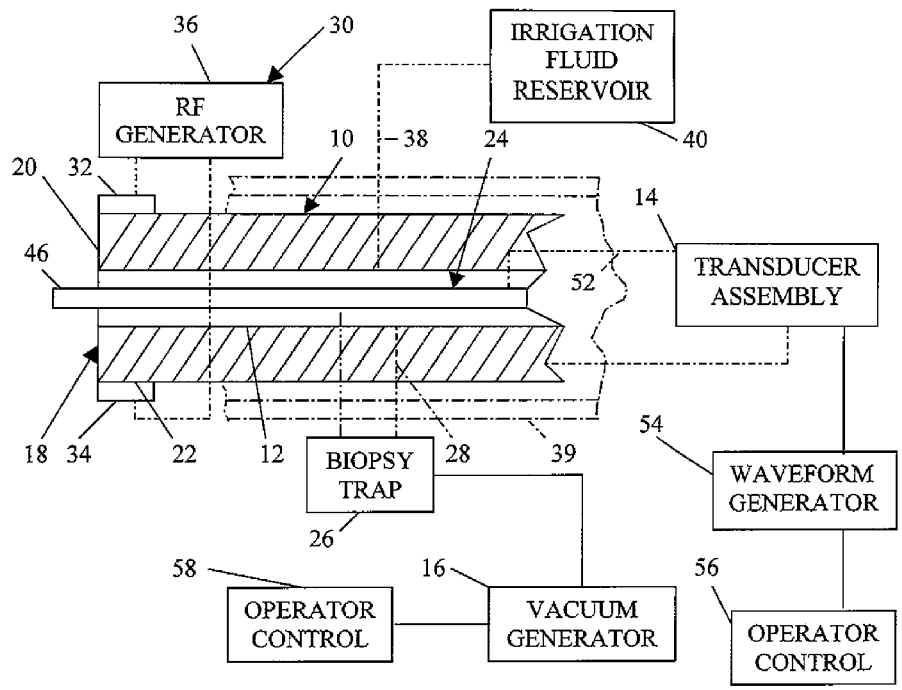
FIG. 1 is partially a schematic longitudinal cross-sectional view of a distal end portion of an ultrasonic surgical device and partially a block diagram of a circuit for driving the device, for use in a tissue excision method in accordance with the present invention.

As depicted in FIG. 1, a surgical apparatus for ablating a target tissue mass TTM (FIG. 2) such a breast or uterine fibroid mass from inside a patient PT (FIG. 2) in a minimally invasive procedure comprises an elongate probe 10, a suction channel 12, a transducer assembly 14 operatively connected to the probe for ultrasonically vibrating the probe, and a vacuum generator or suction source 16. Channel 12 extends longitudinally along the probe and, in a principal embodiment of the surgical apparatus, particularly takes the form of a bore through the probe. Vacuum generator or suction source 16 is operatively connectable to probe 10 so as to apply suction to the channel at a vacuum level greater than 24" Hg to thereby maintain a target tissue mass in engagement with a distal tip 18 of the probe during the vibrating of the probe and enable ablation of at least a selectable portion of the target tissue mass TTM. Probe 10 and transducer assembly 14 are configured so that distal tip 18 of the probe has an excursion amplitude or distance greater than 275 microns. The direction of excursion of distal tip 18 depends on the kind of ultrasonic vibration. Distal tip 18 has an operative surface that is a transverse end face 20 of probe 10 in the case of longitudinal compression waves and a lateral longitudinal surface 22 in the case of transverse shear waves.

A waveform generator 54 responsive to an operator control unit, interface or switches 56 is operatively connected to transducer assembly 14 for transmitting thereto an electrical waveform of appropriate ultrasonic frequency for generating a standing wave in probe 10 to cause distal tip 18 to experience an excursion amplitude or distance greater than 275 microns. Vacuum generator or suction source 16 is operated under user input from an operator control 58.

Figure 2:
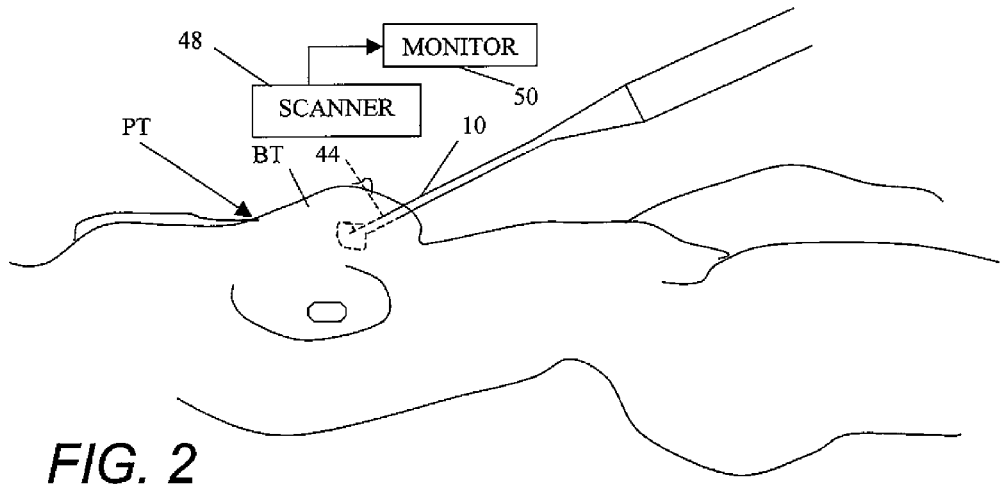
FIG. 2 is a diagram showing use of the device in removing a fibroid mass in a mammary gland of a patient.

As further depicted in FIG. 1, the surgical apparatus optionally includes a cannula 24 insertable through suction channel 12 for extracting a biopsy sample of the target tissue mass TTM while a distal end portion of probe 10 is disposed in the patient PT (see FIG. 2). Alternatively, the extraction of biopsy fragments may be accomplished by a biopsy trap 26 in a suction line 28 communicating with channel 12 to trap tissue during an ultrasonic vibrating of probe tip 18.

The surgical apparatus of FIG. 1 may additionally comprise an electrical circuit 30 for conducting current to distal tip 18 and from the distal tip into tissues of the patient PT to effect a cauterization of bleeding blood vessels (not shown). Electrical circuit 30 may include one or more electrodes 32 and 34 attached to probe 10 in a region about distal tip 18 and a radio-frequency electrical waveform generator 36 that supplies the current to the electrodes to achieve cauterization.

An irrigation conduit 38 and a pressurizable reservoir 40 may be provided for feeding an irrigation fluid to probe tip 18 to enhance cavitation forces, irrigate and cool the operative site and provide a carrier for ablated tissue. Irrigation conduit 38 may define a fluid flow path different from that of channel 12, for example, an annular space about probe 10. In that case a tubular sheath 39 is disposed about probe 10. Alternatively, irrigation conduit 38 may be connected to channel 12 for supplying irrigation fluid to an operative site, e.g., target tissue mass TTM, in alternation with ultrasonic probe vibration.

A surgical method for removing a target tissue mass TTM from a breast BT of patient PT comprises inserting a distal end portion 44 of probe 10 into the patient so that distal tip 18 is in contact with target tissue mass TTM inside the patient. Transducer assembly 14 may be active during the insertion process to facilitate the passing of distal tip 18 through overlying tissues. After contact of distal tip 18 with target tissue mass TTM, transducer assembly 14 is activated to ultrasonically vibrate probe 10 so that distal tip 18 has an excursion amplitude or distance greater than 275 microns. During the vibrating of probe 10, vacuum generator or suction source 16 is operated to apply suction to channel 12 at a vacuum level greater than 24" Hg. This degree of negative or under pressure maintains the target tissue mass TTM in engagement with distal tip 18 during the vibrating of probe 10 and enable ablation of at least a selectable portion of the target tissue mass.

A biopsy sample of target tissue mass TTM may be extracted prior to the application of ultrasonic vibratory energy to the target tissue mass. Vacuum generator or suction source 16 is disconnected from probe 10 to facilitate deployment of biopsy cannula 24. Cannula 24 is inserted into channel 12 and advanced through the channel to insert a distal end or tip 46 of the cannula into target tissue mass TTM. Subsequently cannula 24 is withdrawn from channel 12 and from patient PT, at which juncture vacuum generator or suction source 16 is reconnected to probe 10. The surgeon then removes target tissue mass TTM as described above.

Alternatively, the extracting of a biopsy sample may be accomplished during an ultrasonic ablation procedure through the use of biopsy trap 26. Tissue fragments generated by ultrasonic ablation and extracted in a slurry of irrigation liquid pass through suction line 28 and are captured in trap 25.

During the vibrating of probe 10 by transducer assembly 14, or in intervals between periods of probe activation, electrical current may be conducted from RF generator 36 into the tissues of patient PT cauterize bleeding blood vessels.

During the vibration of probe 10 by a standing wave generated by transducer assembly 14, irrigation fluid is fed to probe tip 18 to enhance cavitation forces, irrigate and cool the operative site and provide a carrier for ablated tissue. The irrigation fluid may include a dissolved additive taken from the group consisting of an anesthetic and an antibiotic. Where irrigation conduit 38 is connected to channel 12 to feed irrigation fluid to distal tip 18 and concomitantly to the operative site, irrigation fluid is conveyed during intervals between successive periods of probe activation.

As diagrammatically shown in FIG. 2, the method may further comprise operating a scanner 48 such as an ultrasound device to scan the patient PT in a region about target tissue mass TTM. Based on the scanning, an image of target tissue mass TTM is produced on a display or video monitor 50, thereby enabling insertion of probe 10 into patient PT and the removal of target tissue mass TTM under indirect visualization.

In an alternate embodiment of the surgical apparatus, the suction channel may surround the probe. In that case, the probe may take the form of a semi-rigid or totally flexible wire or tube (see reference numeral 24) that can be activated by ultrasound energy in lieu of a rigid cannulated probe. This at least partially flexible wire or tube (24) is operatively connected to transducer assembly 14, as indicated at 52 in FIG. 1. The clinician places a standard cannula (reference numeral 10) into the patient PT. The inserting of the distal end portion of the probe (24) into the patient PT includes deploying the probe so that it extends longitudinally through the channel (12) in the introducer cannula (10). The ultrasound wire is advanced to the tumor site. The ultrasound would be turned on and the operation would be performed as describe herein. Such devices may double as the biopsy tool. RF energy and irrigation could also be provided.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A surgical method comprising:
   providing an elongate probe and a suction channel extending longitudinally along said probe;
   inserting a distal end portion of said probe into a breast of a patient so that a distal tip of said probe is in contact with a target fibroid tissue mass inside the patient's breast;
   after contact of said distal tip with the target fibroid tissue mass inside the patient's breast, ultrasonically vibrating said probe so that said distal tip has an excursion amplitude or distance greater than 275 microns;
   during the vibrating of said probe, applying suction to said channel at a vacuum level greater than 24" Hg;
   maintaining the target fibroid tissue mass in engagement with said distal tip during the vibrating'of said probe by virtue of the application of suction to said channel at a vacuum level greater than 24" Hg; and
   ultrasonically ablating at least a selectable portion of the target fibroid tissue mass in response to the vibrating of said probe.

2. The method defined in claim 1, further comprising extracting a biopsy sample of said target fibroid tissue mass while said distal end portion of said probe is disposed in the patient's breast.

3. The method defined in claim 2 wherein the extracting of said biopsy sample includes:
   inserting a biopsy cannula into said channel;
   advancing said cannula through said channel;
   inserting a distal end of said cannula into said target fibroid tissue mass inside the patient's breast;
   subsequently withdrawing said cannula from said channel and from the patient; and
   connecting a suction source to said probe.

4. The method defined in claim 2 wherein the extracting of said biopsy sample includes providing a biopsy trap in a suction line communicating with said channel, thereby trapping tissue during the ultrasonic vibrating of said probe tip.

5. The method defined in claim 1, further comprising conducting electrical current to said distal tip and from said distal tip into tissues of the patient to effect a cauterization of bleeding blood vessels.

6. The method defined in claim 5 wherein the conducting of said electrical current is undertaken simultaneously with the vibrating of said probe.

7. The method defined in claim 1, further comprising feeding an irrigation fluid to said probe tip to enhance cavitation forces, irrigate and cool the operative site and provide a carrier for ablated tissue.

8. The method defined in claim 7 wherein said irrigation fluid includes a dissolved additive taken from the group consisting of an anesthetic and an antibiotic.

9. The method defined in claim 1, further comprising scanning the patient in a region about the target fibroid tissue mass and generating an image of the target fibroid tissue mass on a display, the inserting of said probe into the patient being done under visualization.

10. The method defined in claim 1 wherein said channel is formed as a bore passing longitudinally through said probe, the applying of suction to said channel including providing a suction source connected to said probe.

11. The method defined in claim 1 wherein said channel is formed by a sheath or cannula, the inserting of said distal end portion of said probe into the patient including deploying said probe so that it extends longitudinally through said channel.

* * * * *